US008226668B2

(12) United States Patent
Zeiner et al.

(10) Patent No.: US 8,226,668 B2
(45) Date of Patent: Jul. 24, 2012

(54) TISSUE APPOSITION METHOD AND DEVICE INVOLVING SHEETS WITH INTEGRATED TENSIONING SYSTEM

(75) Inventors: Mark S. Zeiner, Mason, OH (US); Michael J. Stokes, Cincinnati, OH (US); Thomas E. Albrecht, Cincinnati, OH (US); Jason L. Harris, Mason, OH (US); Mark S. Ortiz, Milford, OH (US); Lawrence Crainich, Charlestown, NH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 772 days.

(21) Appl. No.: 12/113,752

(22) Filed: May 1, 2008

(65) Prior Publication Data
US 2009/0275962 A1 Nov. 5, 2009

(51) Int. Cl.
*A61F 2/02* (2006.01)
(52) U.S. Cl. .......................................... 606/151; 600/37
(58) Field of Classification Search .................. 606/151, 606/215, 216, 153; 600/37; 128/898
See application file for complete search history.

(56) References Cited

U.S. PATENT DOCUMENTS

| | | | | |
|---|---|---|---|---|
| 5,697,978 A * | 12/1997 | Sgro | | 623/23.64 |
| 5,919,232 A * | 7/1999 | Chaffringeon et al. | | 424/423 |
| 6,648,921 B2 * | 11/2003 | Anderson et al. | | 623/23.64 |
| 6,652,450 B2 * | 11/2003 | Neisz et al. | | 600/30 |
| 6,746,458 B1 * | 6/2004 | Cloud | | 606/151 |
| 6,971,986 B2 * | 12/2005 | Staskin et al. | | 600/30 |
| 7,083,568 B2 * | 8/2006 | Neisz et al. | | 600/30 |
| 7,160,312 B2 * | 1/2007 | Saadat | | 606/153 |
| 7,175,591 B2 * | 2/2007 | Kaladelfos | | 600/37 |
| 7,628,821 B2 * | 12/2009 | Stack et al. | | 623/23.64 |
| 7,753,870 B2 * | 7/2010 | Demarais et al. | | 604/8 |
| 7,815,562 B2 * | 10/2010 | Chu | | 600/30 |
| 2003/0093117 A1 * | 5/2003 | Saadat | | 606/221 |
| 2005/0192601 A1 * | 9/2005 | Demarais | | 606/151 |
| 2005/0250980 A1 | 11/2005 | Swanstrom | | |
| 2005/0251208 A1 * | 11/2005 | Elmer et al. | | 606/232 |
| 2006/0253142 A1 | 11/2006 | Bjerken | | |
| 2007/0185532 A1 * | 8/2007 | Stone et al. | | 606/232 |
| 2007/0198039 A1 * | 8/2007 | Jones et al. | | 606/151 |
| 2008/0221599 A1 * | 9/2008 | Starksen | | 606/157 |
| 2009/0062850 A1 * | 3/2009 | Ken | | 606/215 |

FOREIGN PATENT DOCUMENTS

| | | |
|---|---|---|
| FR | 2798280 | 3/2001 |
| WO | WO2005/089373 | 9/2005 |
| WO | WO2005/097012 | 11/2005 |
| WO | WO2008/108936 | 9/2008 |

* cited by examiner

*Primary Examiner* — Julian Woo
*Assistant Examiner* — Christopher L Templeton
(74) *Attorney, Agent, or Firm* — Welsh Flaxman & Gitler LLC

(57) ABSTRACT

A tensioning system for restricting the available volume of a gastric cavity includes a base material that is shaped and dimensioned for surgical attachment to surfaces on or within the body. Multiple tensioning members are incorporated into the base material, each of the tensioning members including a first end and a second end, wherein pulling upon the tensioning member will cause edges of the base material to be drawn together. The method for restricting the available volume of a gastric cavity includes securing edges of a tensioning system to the gastric cavity and drawing the edges of the tissue together to create a fold in the tissue.

5 Claims, 18 Drawing Sheets

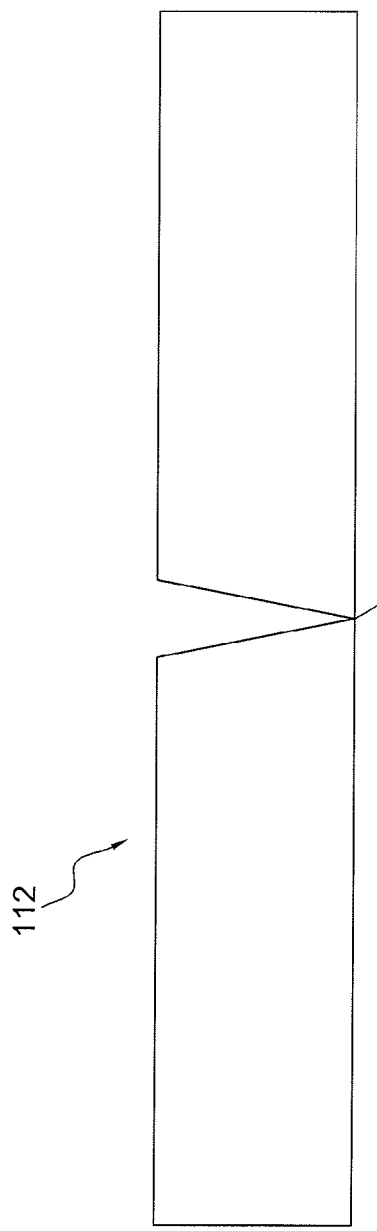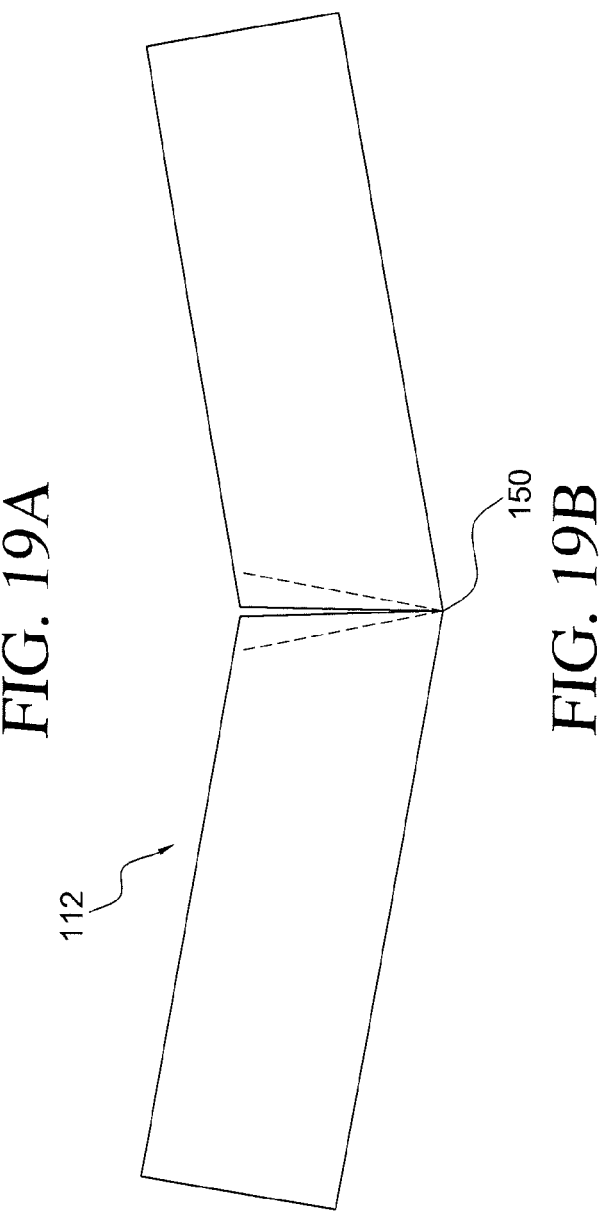
FIG. 19A
FIG. 19B

Typical mesh sold in fabric stores
Material .21mm thick
Mesh pattern diameter approx. 3mm Ethicon Inc. mesh
Material .39mm thick
Mesh pattern diameter approx. 2.5mm

TISSUE APPOSITION METHOD AND DEVICE INVOLVING SHEETS WITH INTEGRATED TENSIONING SYSTEM

BACKGROUND OF THE INVENTION

1. Field of the Invention

The invention relates to a method and device used to appose tissue through the application of a sheet of material with a built in tensioning system. The sheet of material may be secured to the tissue through a variety of mechanisms, and the integrated tensioning system is tightened to bring the sheet of material from an undeployed configuration to the desired deployed configuration.

2. Description of the Related Art

Obesity is a medical condition affecting more than 30% of the population in the United States. Obesity affects an individual's personal quality of life and contributes significantly to morbidity and mortality. Obese patients, i.e., individuals having a body mass index ("BMI") greater than 30, often have a high risk of associated health problems (e.g., diabetes, hypertension and respiratory insufficiency), including early death. With this in mind, and as those skilled in the art will certainly appreciate, the monetary and physical costs associated with obesity are substantial. In fact, it is estimated the costs relating to obesity are in excess of 100 billion dollars in the United States alone. Studies have shown that conservative treatment with diet and exercise alone may be ineffective for reducing excess body weight in many patients. Bariatrics is the branch of medicine that deals with the control and treatment of obesity. A variety of surgical procedures have been developed within the bariatrics field to treat obesity. The most common currently performed procedure is the Roux-en-Y gastric bypass (RYGB). This procedure is highly complex and is commonly utilized to treat people exhibiting morbid obesity. In a RYGB procedure a small stomach pouch is separated from the remainder of the gastric cavity and attached to a resectioned portion of the small intestine. This resectioned portion of the small intestine is connected between the "smaller" gastric cavity and a distal section of small intestine allowing the passage of food therebetween. The conventional RYGB procedure requires a great deal of operative time. Because of the degree of invasiveness, post-operative recovery can be quite lengthy and painful. Still more than 100,000 RYGB procedures are performed annually in the United States alone, costing significant health care dollars.

In view of the highly invasive nature of the RYGB procedure, other less invasive procedures have been developed. These procedures include gastric banding, which constricts the stomach to form an hourglass shape. This procedure restricts the amount of food that passes from one section of the stomach to the next, thereby inducing a feeling of satiety. A band is placed around the stomach near the junction of the stomach and esophagus. The small upper stomach pouch is filled quickly, and slowly empties through the narrow outlet to produce the feeling of satiety. Other forms of bariatric surgery that have been developed to treat obesity include Fobi pouch, bilio-pancreatic diversion and gastroplasty or "stomach stapling".

Morbid obesity is defined as being greater than 100 pounds over one's ideal body weight. For individuals in this category, gastric banding, RYGB or another of the more complex procedures may be the recommended course of treatment due to the significant health problems and mortality risks facing the individual. However, there is a growing segment of the population in the United States and elsewhere who are overweight without being considered morbidly obese. These persons may be 20-30 pounds overweight and want to lose the weight, but have not been able to succeed through diet and exercise alone. For these individuals, the risks associated with the RYGB or other complex procedures often outweigh the potential health benefits and costs. Accordingly, treatment options should involve a less invasive, lower cost solution for weight loss.

It is known to create cavity wall plications through endoscopic only procedures. However, operating solely within the interior of the gastric cavity limits the plication depth that can be achieved without cutting. Furthermore, access and visibility within the gastric and peritoneal cavities is limited in a purely endoscopic procedure as the extent of the reduction increases.

With the foregoing in mind, it is desirable to provide surgical weight loss procedures (and associated medical instruments) that are inexpensive, with few potential complications, and that provide patients with a weight loss benefit while buying time for the lifestyle changes necessary to maintain the weight loss. Further, it is desirable that the procedure be minimally invasive to the patient, allowing for a quick recovery and less scarring. The present invention provides such a procedure and medical instruments.

SUMMARY OF THE INVENTION

It is, therefore, an object of the present invention to provide a tensioning system for restricting the available volume of a gastric cavity. The tensioning system includes a base material that is shaped and dimensioned for surgical attachment to surfaces on or within the body. Multiple tensioning members are incorporated into the base material, each of the tensioning members including a first end and a second end, wherein pulling upon the tensioning member will cause edges of the base material to be drawn together.

It also an object of the present invention to provide a tension system wherein the tensioning members are strings that are parallel to one another and spaced along one length of the base material such that each of the tensioning members principally extends along either a length or width of the sheet.

It another object of the present invention to provide a tension system wherein the base material is a woven sheet of material and each of the tensioning members is woven within the sheet such that a woven central portion of the tensioning member is free to move relative to the sheet.

It a further object of the present invention to provide a tension system wherein each of the tensioning members is woven so as to extend from one side of the sheet with the first end and the second end of the tensioning member extending from opposite sides of the sheet such that pulling upon either or both of the first end and the second end will cause edges of the sheet to be drawn together.

It also an object of the present invention to provide a tension system wherein the first end of each of the tensioning members is fixed and pulling the second end of the tensioning member will bring the edges of the sheet.

It another object of the present invention to provide a tension system wherein the base material is a bar to which tensioning members are secured.

It is also an object of the present invention to provide a tension system wherein the base material is a sheet of material and the sheet of material is provided with a zipper for drawing the edges thereof together.

It a further object of the present invention to provide a method for restricting the available volume of a gastric cavity including securing edges of a tensioning system to the gastric cavity and drawing the edges of the tissue together to create a fold in the tissue.

Other objects and advantages of the present invention will become apparent from the following detailed description when viewed in conjunction with the accompanying drawings, which set forth certain embodiments of the invention.

BRIEF DESCRIPTION OF THE DRAWINGS

FIGS. 19A and 19B are close up views of a living hinge type joint incorporated into the mesh sheet of material to allow bending in a controlled direction.

DESCRIPTION OF THE PREFERRED EMBODIMENTS

Figure 1:
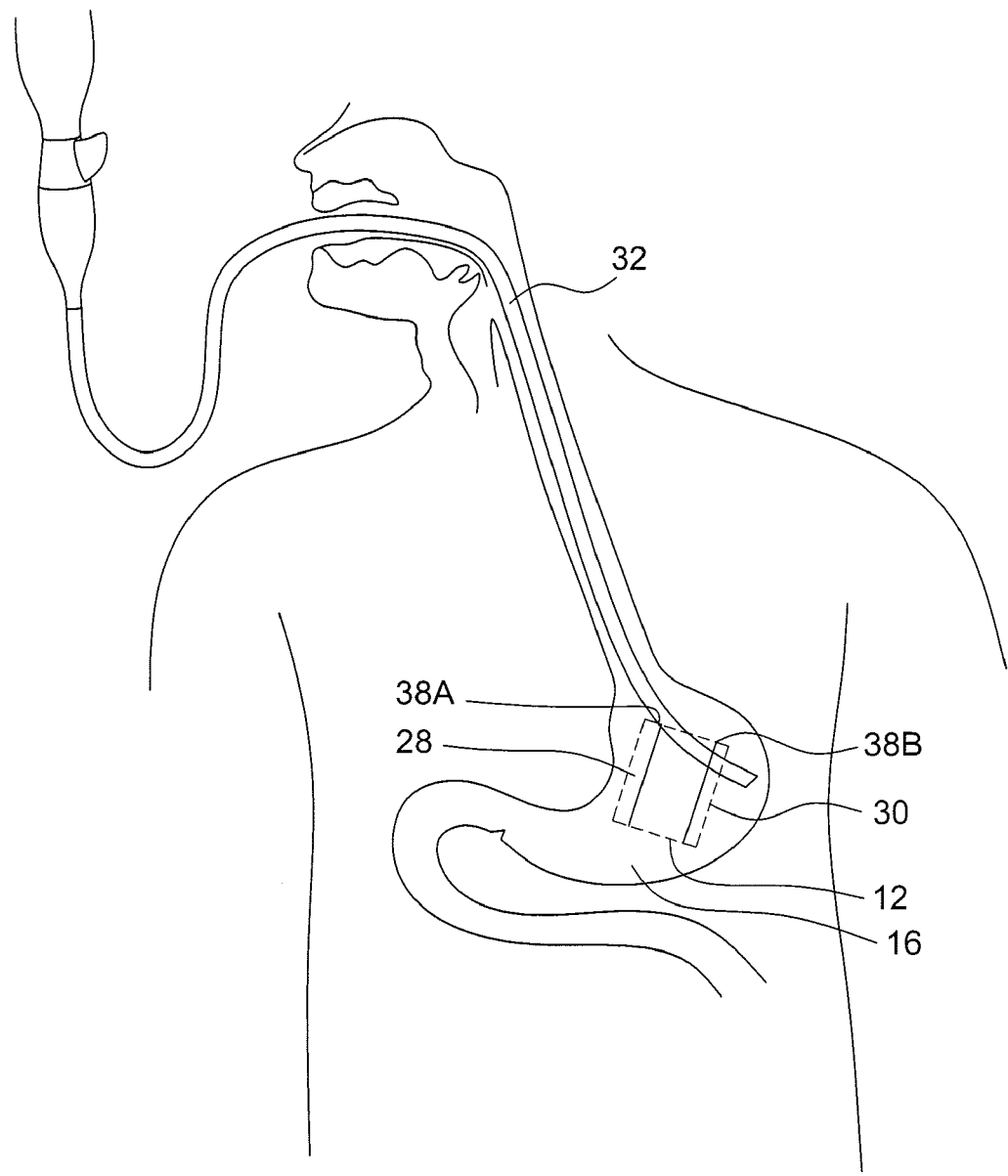
FIG. 1 is a schematic view of a gastric cavity and gastroscope showing placement of mesh sheet of material in the stomach.

The detailed embodiments of the present invention are disclosed herein. It should be understood, however, that the disclosed embodiments are merely exemplary of the invention, which may be embodied in various forms. Therefore, the details disclosed herein are not to be interpreted as limiting, but merely as a basis for teaching one skilled in the art how to make and/or use the invention.

As discussed above in the Background of the Invention section, obesity is becoming a growing concern, particularly in the United States, as the number of obese people continues to increase, and more is learned about the negative health effects of obesity. Morbid obesity, in which a person is 100 pounds or more over ideal body weight, in particular poses significant risks for severe health problems. Accordingly, a great deal of attention is being focused on treating obese patients.

One method of treating morbid obesity is to restrict the available volume of the gastric cavity in order to limit food consumption and provide an earlier feeling of satiety. Although the present invention is described herein for use in conjunction with the treatment of obesity through gastric reduction, it is contemplated the concepts underlying the present invention has many applications related to bariatric (initial or revisional) surgical therapies.

Referring to FIGS. 1, 2 and 10-14, in its most basic form the present invention is composed of a tensioning system 10 in the form of a base material which in accordance with a first embodiment is a mesh sheet of material 12 that is shaped and dimensioned for surgical attachment (stapled, sutured, glued, etc.) to surfaces on or within the body via attachment elements 40 which may be staples, sutures, adhesives, etc. For example, and as disclosed in accordance with a preferred embodiment, to the interior wall 14 (mucosal) or exterior wall 15 (serosal) of the gastric cavity 16 by way of attachment elements 40. Incorporated into the sheet 12 are multiple tensioning members 18 preferably composed of strings 20 (e.g. suture) that are parallel to one another and spaced along one length of the sheet 12 such that each of the tensioning members 18 principally extends along either a length or width of the sheet 12.

Each tensioning member 18 includes a first end 22 and a second end 24. Each tensioning member 18 is attached to the sheet 12 (woven through the sheet in multiple places, covered by other material creating a channel, etc.), but contains portions that can slide relative to the sheet 12 in the direction of the length of the tensioning member 18. In accordance with a preferred embodiment of the present invention, the tensioning member 18 is woven within the sheet 12 such that the woven central portion 26 of the tensioning member 18 is free to move relative to the sheet 12. The tensioning member 18 is woven so as to extend from one side of the sheet 12 with the first end 22 and the second end 24 of the tensioning member 18 extending from opposite sides of the sheet 12 such that pulling upon either or both of the first end 22 and second end 24 will cause the edges 28, 30 of the sheet 12 (positioned at line 38A and line 38B) to be drawn together. Both the first end 22 and the second end 24 of the tensioning member 18 may run through a knotting element 23 and extend beyond, or away from, the respective first and second edges 28, 30 of the sheet 12 for engagement and actuation in accordance with concepts underlying the present invention and as discussed below in greater detail. The desired effect is such that when both the first end 22 and the second end 24 of the tensioning member 18 are pulled together and cinched by knotting element 23, the opposed edges 28, 30 of the sheet 12, which the tensioning member 18 extend between, are brought together. Once the opposed edges 28, 30 of the sheet 12 are drawn together in a desired manner, further tension on the tensioning member 18 serves to cinch the sheet 12 together reducing the diameter of the resulting loop of sheet 12. This is very similar to the concept of "draw-strings" that are common in many items of daily use (trash bags, clothing, purses, etc.). Once performed, the result of cinching the first end 22 and second end 24 of the tensioning member 18 together is to transform a sheet 12 that was initially flat into a cylindrical structure with opposed edges 28, 30 of the sheet 12 in alignment.

As shown with reference to FIGS. 11 and 12 and FIGS. 13 and 14, the manner in which the suture 20 is woven to the sheet 12 determines how the fold is formed. For example, and with reference to FIGS. 11 and 12, where the suture 20 is only woven to the sheet 12 along the edges 28, 30 thereof, the sheet 12 will follow the contour of the fold. Another way to achieve this result is by attaching the sheet to the tissue in the region between the edges. Where the suture 20 is woven across the full length of the sheet 12, the sheet will bunch up as the edges 28 are drawn together (see FIGS. 13 and 14).

Figure 15:
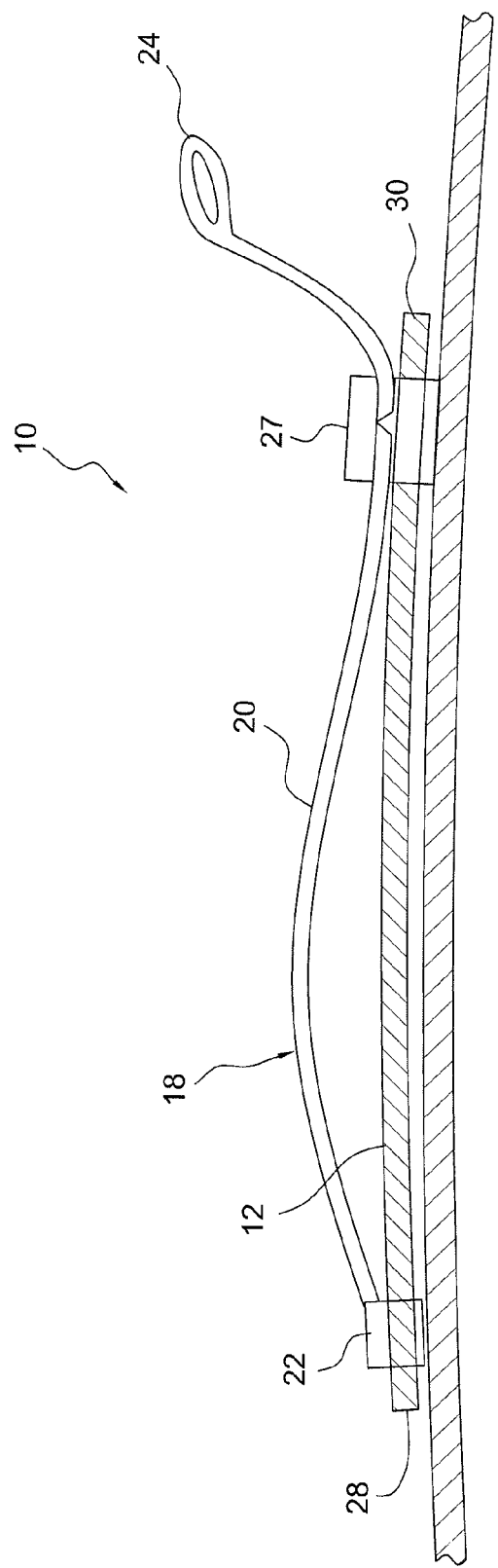
FIG. 15 is a side elevation view showing an alternate tension system for the mesh sheet of material.

In accordance with an alternate embodiment, and with reference to FIG. 15, a simple modification to the embodiment described with reference to FIGS. 1, 2 and 10-14, is to fix the first end 22 (or the second end in accordance with an alternate embodiment) of a tensioning member 18 at or near the edge 28, 30 of the sheet 12. If a sheet 12 is surgically attached to a tissue surface with the tensioning members 18 (that is, the various strings employed in accordance with the present invention) incorporated in this configuration, pulling the free second end 24 of the tensioning member 18 through a locking element 27 fixed near edge 30 will bring the edges 28, 30 of the sheet 12 together. Such an embodiment can be used to approximate two locations of interest if the sheet 12 is attached so that the exit point and the fixation point of the tensioning member 18 to the sheet 12 are attached at or near the two locations of interest on the surface(s). Locking element 27 functions to lock string 20 along its length as it is pulled therethrough.

The embodiments described with reference to FIGS. 1, 2 and 10-14 and with reference to FIG. 15, can be combined to create a multitude of deployed tissue configurations. Ideal device configurations will vary with the intended procedure. However, it is believed the present tissue apposition system has two main roles in surgery; to temporarily hold tissue in place for other procedural steps after which time it is removed, and alternatively as a "permanent" (is not surgically removed, but may degrade/absorb over time) scaffold for fixation support that is secured and left in place. Temporary and permanent applications include, but are not limited to, approximating tissues into new configurations, closing surfaces for healing, partitioning/sealing off cavities, restricting access within a cavity/lumen, and providing structural support to adjacent tissues.

As briefly mentioned above, the sheet is preferably mesh. Mesh offers numerous advantages: tissue may heal through the mesh leaving a more durable result; strings are easily woven throughout a mesh; mesh serves as a permeable membrane. Embodiments where the sheet is a mesh-like material are predominantly described below, but in virtually all cases a solid sheet of material can be used in place of a mesh.

As discussed above, tissue is brought together from two locations and incorporated into a new configuration. An example of a bariatric application is gastric volume reduction. In one method of gastric volume reduction, stomach volume may be reduced by bringing together two lines of tissue, one along the greater curve and one along the lesser curve on the anterior surface of the stomach. In accordance with a preferred embodiment of the present invention, available stomach volume may be restricted by forming one or more folds in the anterior wall of the gastric cavity (creating a serosa-to-serosa fold). The folds reduce the outer surface area of the stomach and, correspondingly, the available food volume within the gastric cavity. In accordance with one restriction technique, available stomach volume is restricted by forming a single, longitudinally extending fold along the anterior wall of the gastric cavity. The fold extends the full length of the anterior wall of the gastric cavity between the fundus and the pylorus. Alternatively, a shorter fold may be formed depending upon the desired amount of gastric volume reduction.

Generally, to form a fold in accordance with the present invention, a flexible gastroscope 32 is passed transesophageally into the gastric cavity 16 as shown in FIG. 1. The gastroscope 32 provides insufflation, illumination, and visualization of the gastric cavity 16, as well as a passageway into the gastric cavity 16 for the insertion and use of other endoscopic instruments. The gastric cavity 16 is first insufflated to create a sufficient rigid working surface along the gastric cavity 16 such that it may be pierced without damaging the opposing wall of the stomach. Insufflation of the gastric cavity 16 may also allow the boundaries of the gastric cavity 16 and the desired location for a fold 34 to be mapped out by external palpation. The pressure on the abdominal wall 36 is observed within the gastric cavity 16 through the gastroscope 32 to also determine the appropriate placement of one or more trocars (or other ports allowing abdominal access) for completion of the procedure in accordance with the present invention.

After the gastric cavity 16 has been mapped through the gastroscope 32, and locations for a preferred fold location are determined, the sheet 12 in accordance with the present invention is deployed and attached to the interior wall 14 (see FIGS. 11 and 12) or exterior wall (see FIGS. 13 and 14) of the gastric cavity 16 for the formation of a fold in accordance with the present invention. More particularly, for minimally invasive laparoscopic procedures and virtually all endoscopic procedures, for example, in the performance of gastric reduction surgery, it will be necessary to deliver the mesh sheet 12 through small openings potentially over long distances to the surgical site. One general class of solutions is to package a mesh sheet 12 in a first configuration which is compressed into a delivery system (small tube or similar) where it can be delivered to the surgical site. Delivery methods include endoscopic procedures and/or laparoscopic approaches (preferably using 3-5 mm trocars). The approach depends on whether the mesh sheet 12 is to be applied on the inside of the gastric cavity 16 or on the outside.

To start, the mesh sheet 12 is preferably positioned in the surgical site and ejected from the delivery tube and unfolded into the expanded second configuration using graspers or other tools. Once unfolded the sheet 12 is placed on the tissue and is securely attached along the edges 28, 30 thereof on the lines 38A and 38B, respectively (FIGS. 1 and 2), as described in more detail below. The location of edges 28, 30 should correspond to the lines of tissue to be brought together.

In accordance with an alternate embodiment, the mesh sheet 12 is wrapped around the distal portion of the endoscope during flexible endoscopy. Once the endoscope is within the gastric cavity 16 (or other location of interest), the mechanism keeping the mesh held in place along the endoscope is released and the mesh is freely removed and unrolled.

Although laparoscopic delivery for use in gastric reduction surgery is disclosed herein for the purpose of presenting an understanding of the present invention, it is contemplated the present tension system may be employed in a variety of environments and delivery will therefore be adapted to accommodate these differing applications. For example, for external use, open surgical applications, and some laparoscopic procedures, the mesh sheet can be simply removed from its packaging and may often be manually delivered to the site with or without the aid of standard surgical instruments.

Figure 2:
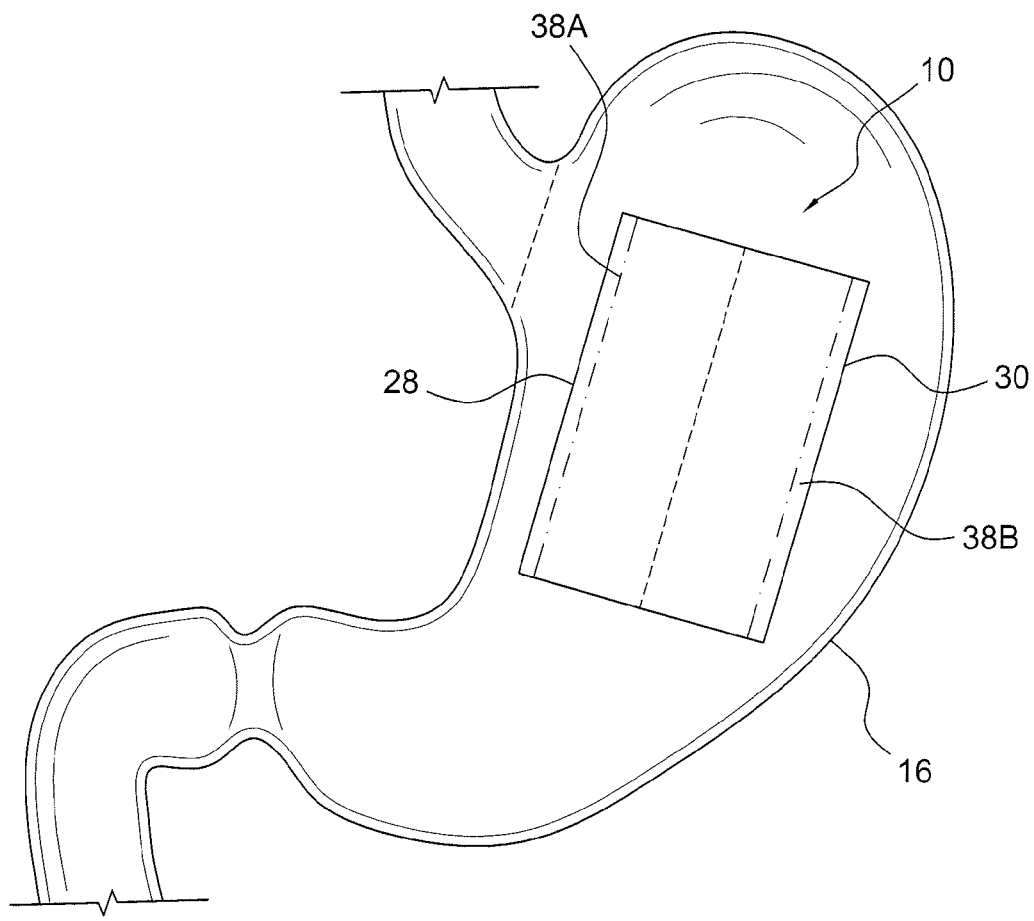
FIG. 2 is a close up of the stomach showing placement of a mesh sheet of material in the stomach.

In accordance with a preferred embodiment, and as shown with reference to FIGS. 1 and 2, the mesh sheet 12 is in the shape of a rectangle or square with coupling line 38A, 38B, running vertically on each of the left and right hand sides of the mesh sheet 12. The line on the left is line 38A and the line on the right is line 38B. There are equally spaced points along each of these lines 38A, 38B on the left and right that are connected with a series of pre-tied tensioning members 18 such that the tensioning members 18 can be selectively pulled to bring line 38A and line 38B together, and ultimately bring the attached tissue together. The lines 38A, 38B can be color coded so the surgeon knows where to place the fasteners used in securing the sheet to the tissue. In accordance with a preferred embodiment, the sheet 12 is attached to the tissue using clips, staples, or any other suitable fastener means 40.

Graspers are then used to pull on the series of tensioning members 18. As the tensioning members 18 are pulled and tension is placed on lines 38A and 38B the tissue secured along lines 38A and 38B is juxtaposed together. By using multiple fasteners 42 to secure the folded tissue once lines 38A and 38B are drawn together along line 38A and line 38B, the force is spread out upon all the fasteners 42 along the junction line reducing the possible surgical failure.

The tensioning members 18 are preferably woven through the mesh of the sheet in the following manner: first the mesh is folded back and forth with a folding tool, then a needle is passed through the folded area creating a woven line of suture across the mesh. This technique has been used in surgery for quite some time to create a purse string around the perimeter of an anastomosis. It is contemplated that for some configurations of the tensioning member 18 with respect to the sheet 12 a simple loop connection on each edge of the mesh sheet is adequate and the woven configuration is not needed. It is contemplated many different configurations of folding are possible using these methods and the exact manner of incorporating the tensioning members into the mesh sheet may be varied without departing from the spirit of the present invention. For example, it is contemplated it might be feasible to pull tissue further than ever thought possible using this mesh apposition method.

Alternate configurations are possible to allow more complex tissue folding of more than two lines of tissue. For example, see FIGS. 3 to 9. These figures describe how a double fold technique can be mapped out with a single piece of mesh and multiple tensioning members. The mesh can be manipulated in many directions using loops of tensioning members or locking features that operate similar to a wire tie.

Figure 3:
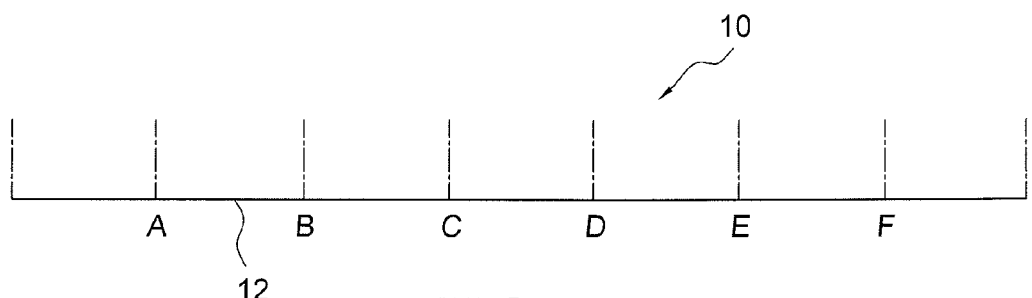
FIG. 3 is a schematic sketch showing the initial mesh sheet of material configuration for a double fold as shown in FIG. 9.
Figure 4:
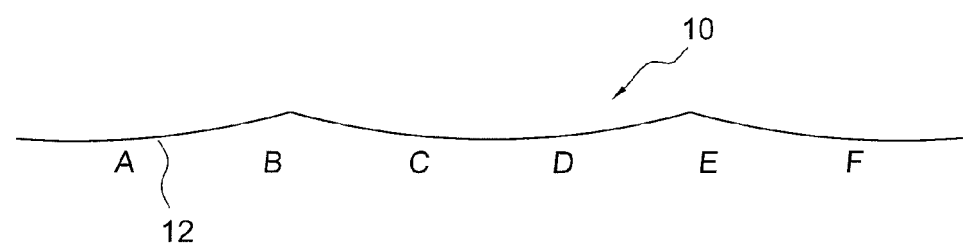
FIG. 4 is a schematic sketch showing step two of the partially folded mesh sheet of material.
Figure 5:
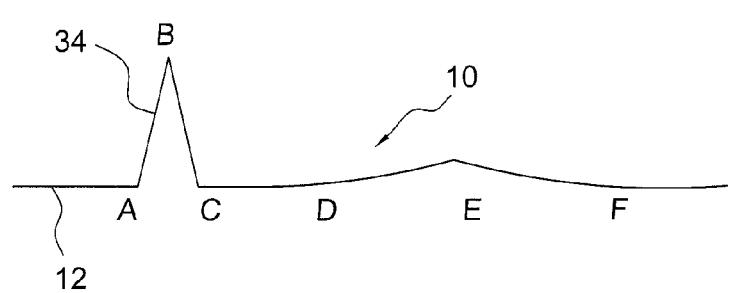
FIG. 5 is a schematic sketch showing step three of the partially folded mesh sheet of material.
Figure 6:
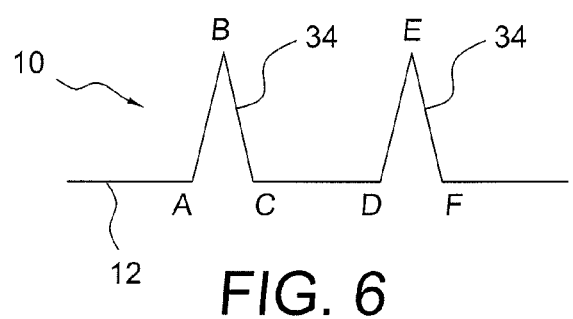
FIG. 6 is a schematic sketch showing step four of the partially folded mesh sheet of material.
Figure 7:
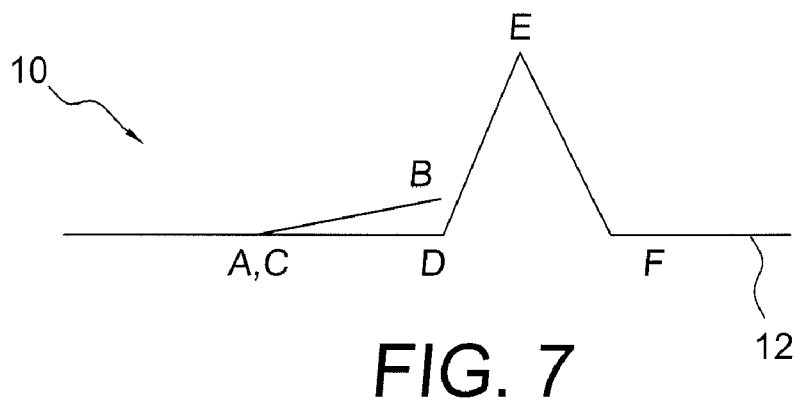
FIG. 7 is a schematic sketch showing step five of the partially folded mesh sheet of material.
Figure 8:
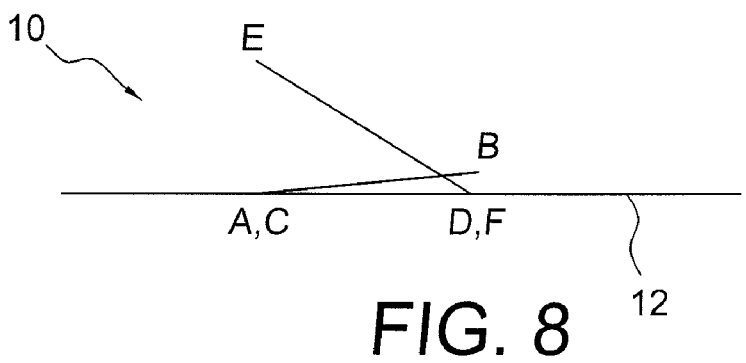
FIG. 8 is a schematic sketch showing step six of the partially folded mesh sheet of material.
Figure 9:
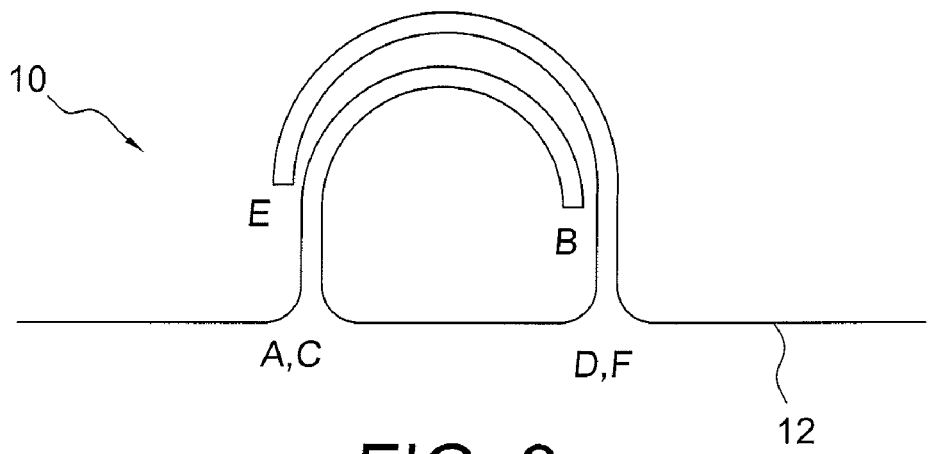
FIG. 9 is a sketch showing the final fold configuration of the double fold created using the method shown in FIGS. 3-8.
Figure 10:
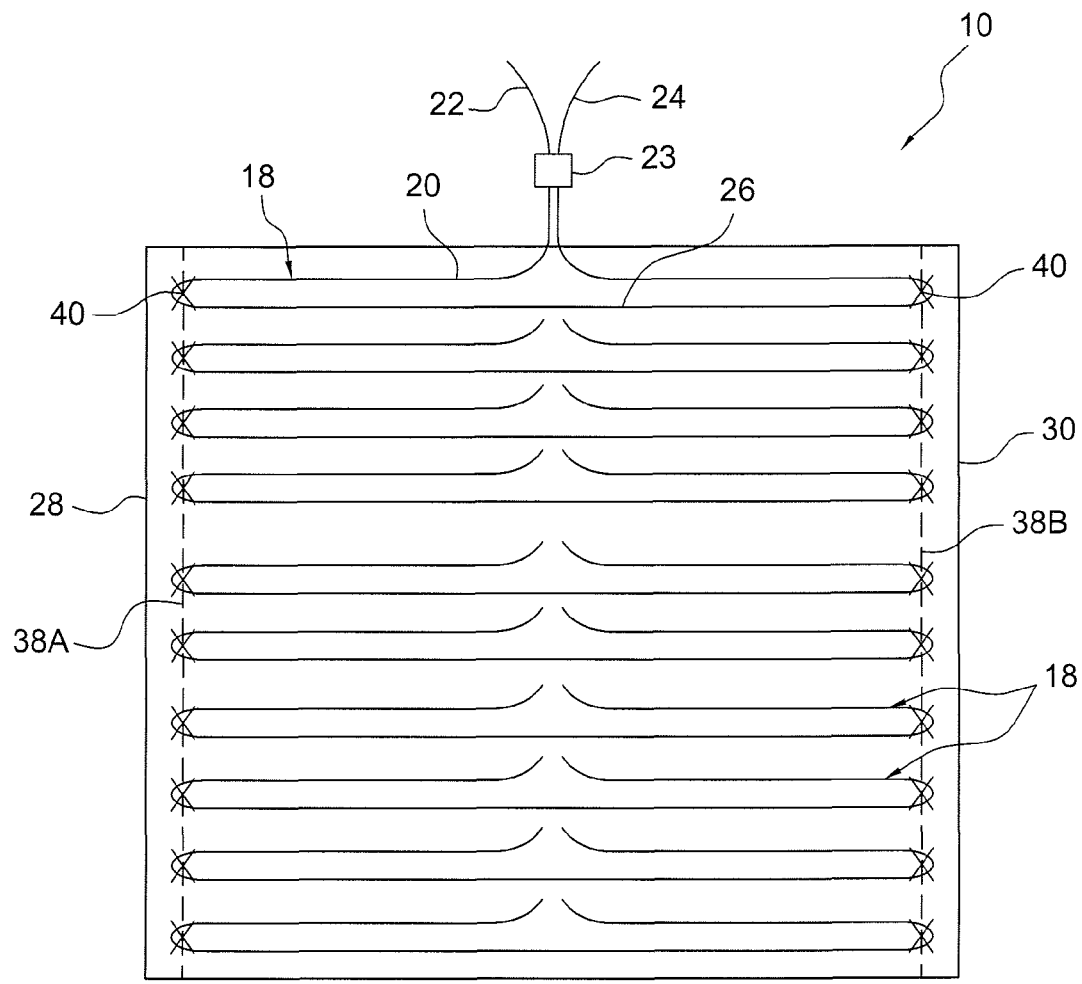
FIG. 10 is a sketch showing the overall top view of the mesh sheet of material in its expanded configuration.
Figure 11:
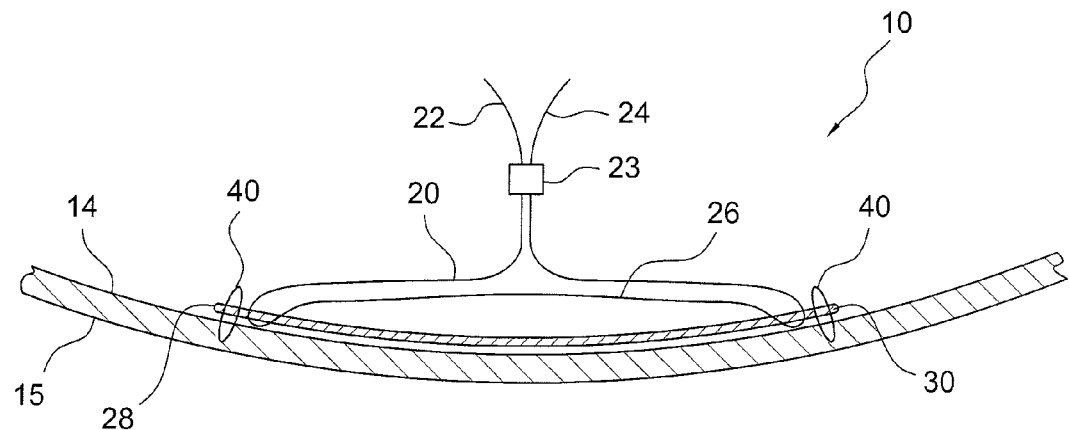
FIG. 11 is a side elevation view showing the mesh sheet of material attached to the stomach wall.
Figure 12:
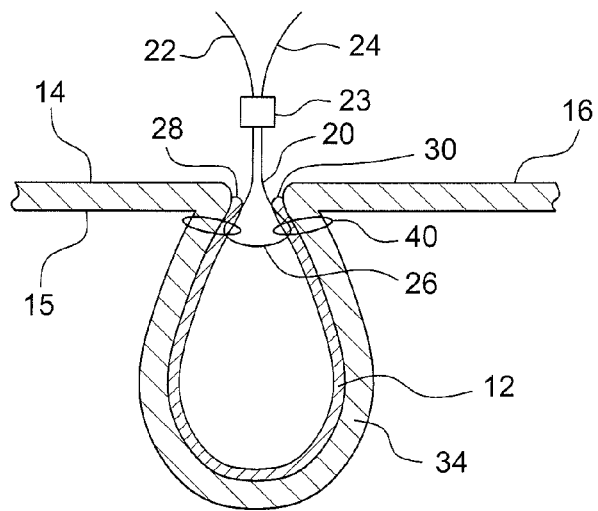
FIG. 12 is a side elevation view showing the mesh sheet of material in a sleeve configuration inside the stomach wall.
Figure 13:
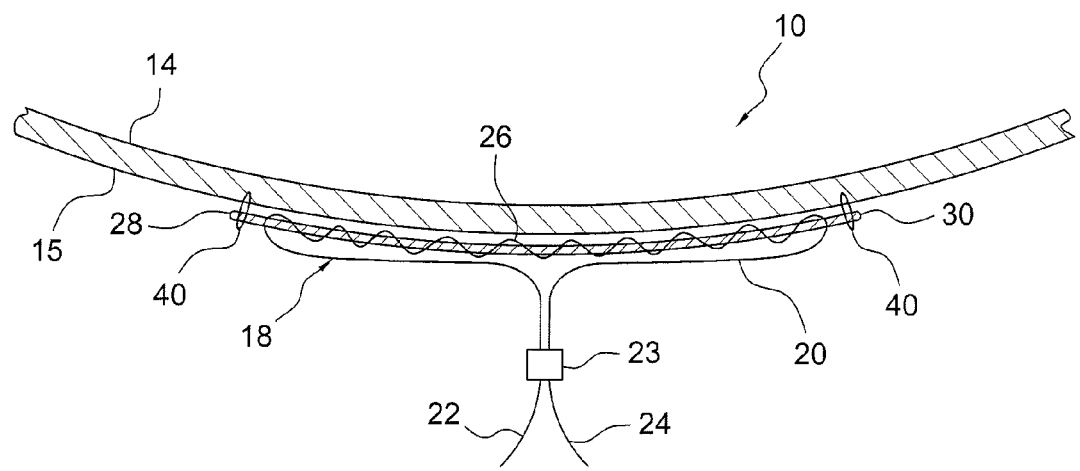
FIG. 13 is a side elevation view showing the mesh sheet of material attached to the outside of the stomach prior to tension member tightening.
Figure 14:
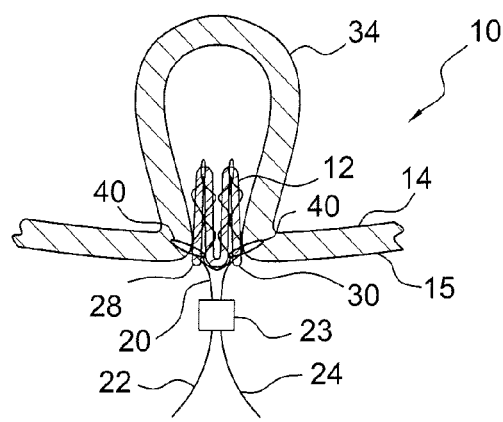
FIG. 14 is a side elevation view showing the mesh sheet of material attached to the outside of the stomach after the tension member is tightened.

More particularly, a sheet of mesh material is laid across a desired tissue surface. Thereafter, the mesh is fastened to the tissue surface along lines A, C, D and F as shown in FIG. 3. Thereafter, and with references to FIGS. 4 to 9 line A is drawn toward line C to create a fold where B is the apex thereof. Also, line D is drawn to line F to create a fold where line E is the apex thereof The fold A, B, C is folded laterally toward the junction of lines D and F and the fold D, E, F is similarly folded toward the junction of lines A and C. Thereafter, line B is secured to the tissue at junction D, F, while line E is secured to the tissue at junction A, C so as to create a double fold in the desired tissue.

In accordance with a preferred embodiment of the present invention, suture and knotting elements may be used as the tensioning members. A piece of suture can be woven through the mesh and placed in a pre positioned location such that the suture loop can be used to bring desired parts of the tissue together. Any number of alternate materials and or locking mechanism may be used without altering the concept underlying the present invention. Other alternate materials might be nylon strips, TEFLON, a synthetic resinous fluorine-containing polymer, PDS, VICRYL, a polyglaactin synthetic absorbable material, PLA.

The results of vertical sleeve gastroplasty are well document and consistently yield acceptable weight loss results. Devices and procedures that more easily and less invasively imitate this surgical intervention are promising. Current devices that try to reach this aim have several issues that using a sheet/mesh may help to resolve. Current sleeve designs are difficult to secure in place and are often difficult to remove. This disclosure allows a rectangular shaped piece of mesh sheet to be secured within the stomach using fasteners such as staples, clips or other means and then reconfigured into the shape of a tube or sleeve that allows food to pass along inside this tube. The mesh sheet would be positioned so that the resulting tube is immediately adjacent to the gastroesophageal junction. In this configuration the mesh acts as an internal sleeve. This would also help to distribute the load on the mesh sheet and not the tissue. The sleeve could be made from bioabsorbable materials so it would not need to be removed.

Figure 17:
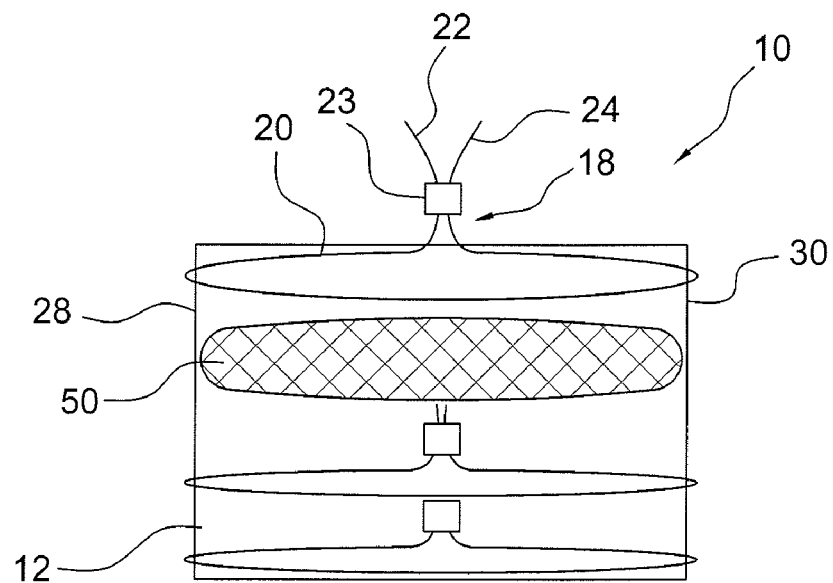
FIGS. 17 and 18 are respectively a top plan view and a sectional view of a tensioning system in accordance with an alternate embodiment of the present invention.
Figure 18:
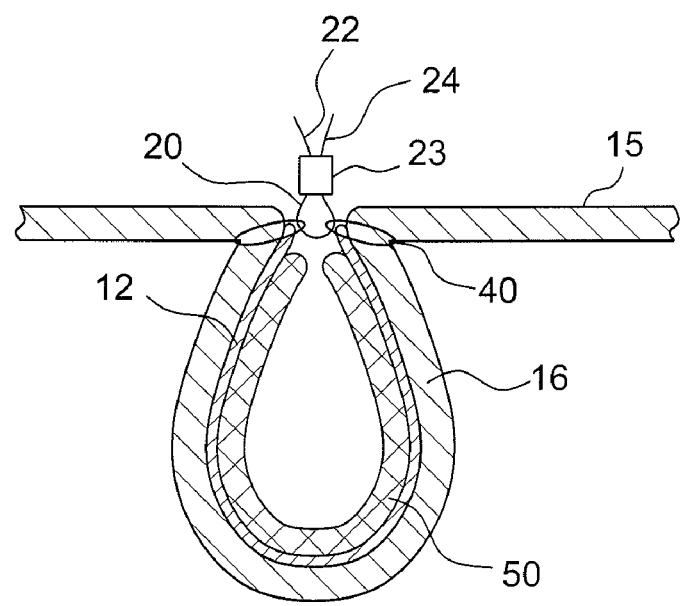
Figure 20:
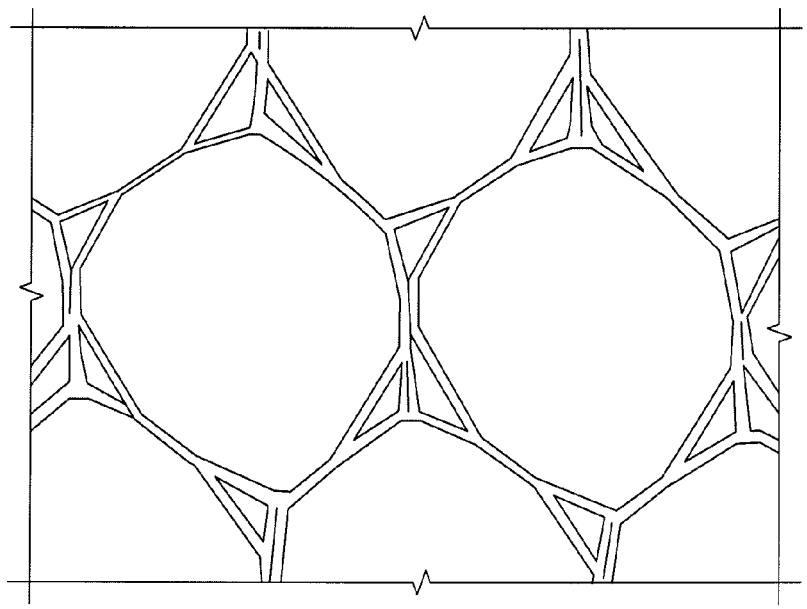
FIG. 20 is a typical mesh sold in fabric stores for reference.
Figure 21:
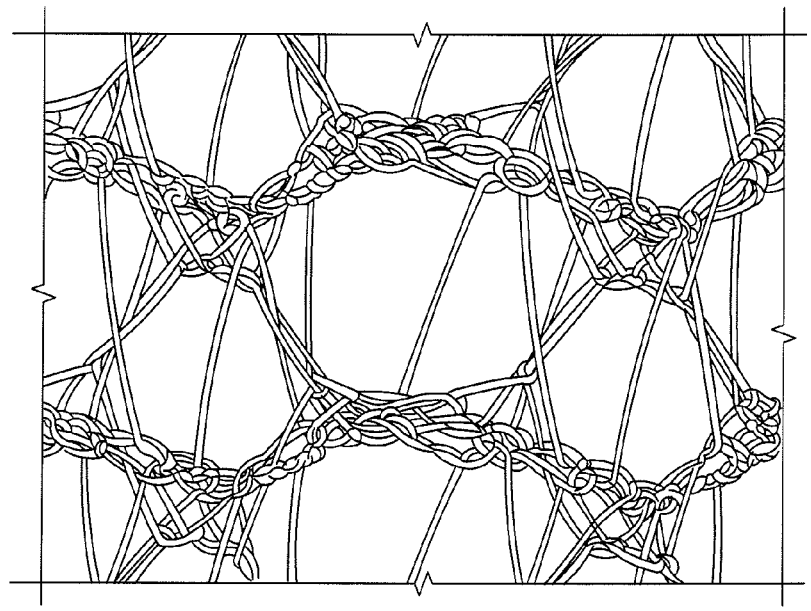
FIG. 21 is a medical mesh sold by Ethicon Inc. for reference.

The sleeve can be designed to "bunch up" along the length of the sleeve creating regions along the length with smaller diameters and others with larger diameters. The smaller diameters will serve to restrict the flow of food more than the larger ones and should provide an additional weight loss benefit as the value of restrictive procedures is documented. To further restrict, predictably size, and allow for adjustment of the diameter of the restriction, an inflatable band may be attached to the mesh sheet within the lumen of the sleeve. This band is ideally attached before the mesh sheet is rolled into a sleeve, and may even be initially attached to the mesh. In either case, once the mesh is cinched into a sleeve, the band is inflated to the desired size creating a restriction within the sleeve that can be adjusted to the desired size. The concept for the design of the band is to closely mimic existing gastric banding technology and can contain any or all of the features that allow for easy and multiple adjustments of its size (ports, smart needles, smart ports, auto adjust features, etc). More particularly, and with reference to FIGS. 17 and 18, an inflatable band 50 is incorporated into the tension system 10 described above. As with the prior embodiment, a tensioning system 10 in the form of a mesh sheet of material 12 that is shaped and dimensioned for surgical attachment (stapled, sutured, glued, etc.) to surfaces on or within the body for example, and as disclosed in accordance with a preferred embodiment, to the interior wall 14 (mucosal) or exterior wall 15 (serosal) of the gastric cavity 16. Incorporated into the sheet 12 are multiple tensioning members 18 preferably composed of strings 20 (e.g. suture) that are parallel to one another and spaced along one length of the sheet 12 such that each of the tensioning members 18 principally extends along either a length or width of the sheet 12.

Each tensioning member 18 includes a first end 22 and a second end 24. Each tensioning member 18 is attached to the sheet 12 (woven through the sheet in multiple places, covered by other material creating a channel, etc.), but contains portions that can slide relative to the sheet 12 in the direction of the length of the tensioning member 18. In accordance with a preferred embodiment of the present invention, the tensioning member 18 is woven within the sheet 12 such that the woven central portion 26 of the tensioning member 18 is free to move relative to the sheet 12. The tensioning member 18 is woven so as to extend from one side of the sheet 12 with the first end 22 and the second end 24 of the tensioning member 18 extending from opposite sides of the sheet 12 such that pulling upon either or both of the first end 22 and second end 24 will cause the edges 28, 30 of the sheet 12 to be drawn together. Both the first end 22 and the second end 24 of the tensioning member 18 extend beyond, or away from, the respective first and second edges 28, 30 of the sheet 12 for engagement and actuation in accordance with concepts underlying the present invention and as discussed below in greater detail. The desired effect is such that when both the first end 22 and the second end 24 of the tensioning member 18 are pulled together, the opposed edges 28, 30 of the sheet 12, which the tensioning member 18 extend between, are brought together. Once the opposed edges 28, 30 of the sheet 12 are drawn together in a desired manner, further tension on the tensioning member 18 serves to cinch the sheet 12 together reducing the diameter of the resulting loop of sheet 12. This is very similar to the concept of "draw-strings" that are common in many items of daily use (trash bags, clothing, purses, etc). Once performed, the result of cinching the first end 22 and second end 24 of the tensioning member 18 together is to transform a sheet 12 that was initially flat into a cylindrical structure with opposed edges 28, 30 of the sheet 12 in alignment.

Figure 16:
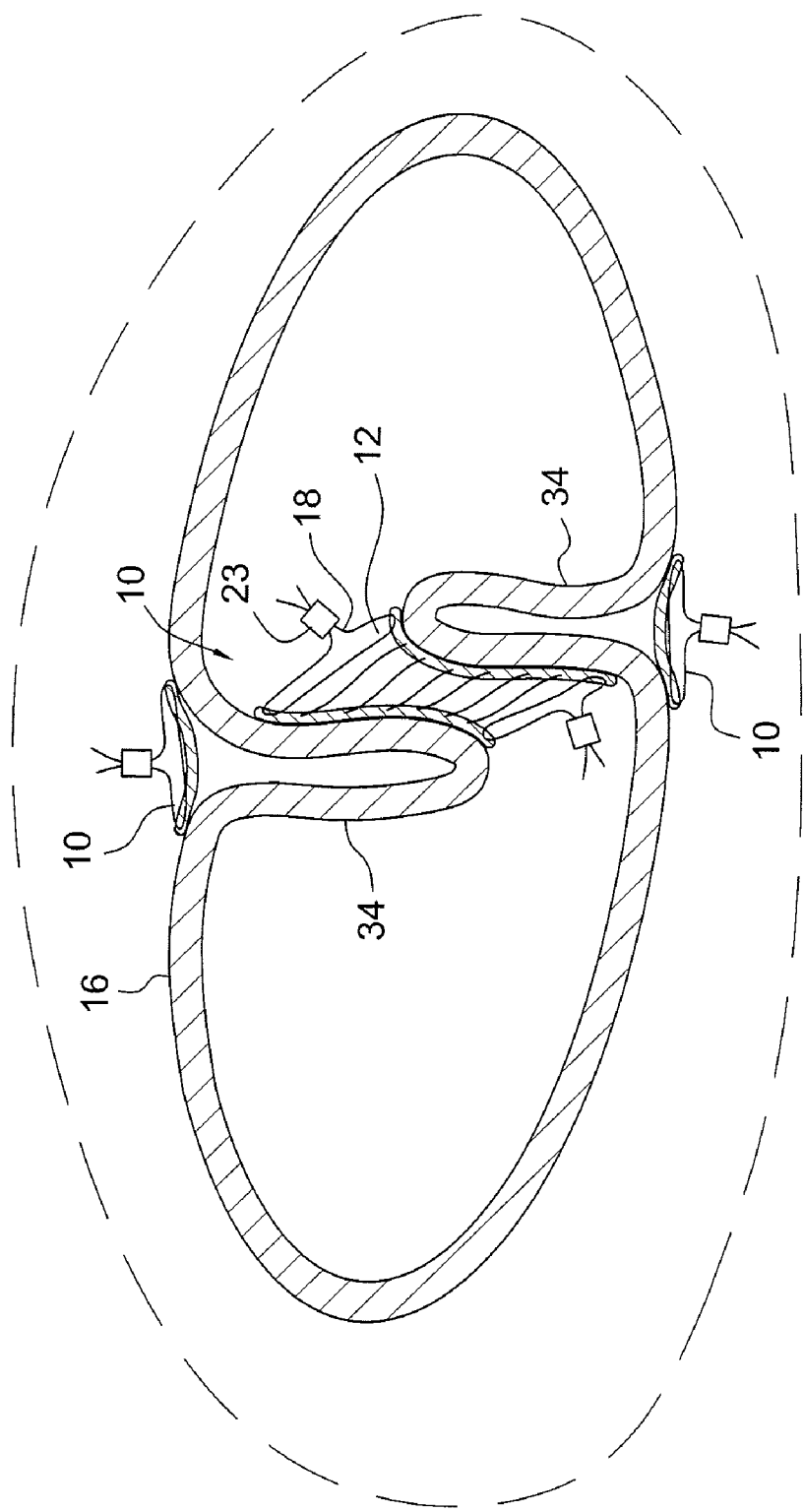
FIG. 16 is a sectional view of the stomach showing a vertical gastroplasty created with mesh sheet of material in accordance with the present invention (the original size of the gastric cavity is shown in broken lines).

Also attached to the mesh sheet 12, and in alignment with the tensioning members 18 is a the inflatable band 50. As such, and as discussed above, when the tensioning members 18 are pulled to draw the opposed edges 28, 30 together, the inflatable band 50 is inflated (for example, via a remote pressure source coupled thereto) bladder may be inflated to control the size of the restriction as desired by the medical practitioner. Referring to FIG. 16, the present tension system 10 may also be used in the formation of folds 34 in the gastric cavity 16. For example, first and second tissue folds or plications 34 are made first using the present tensioning system 10. Then another tensioning system composed of sheet 12 with tensioning member 18 secured thereto is attached to the sides of each plication 34. The two plications 34 each having the mesh sheet 12 attached to the proper side of the fold 34 are then pulled together with tensioning members 18 and a knotting element 23 is applied.

For some applications it may be desirable to provide the mesh sheet with a material anisotropy to induce preferential bending in one direction over another or to keep dimensions in one direction fixed relative to another. One method to accomplish this is to add reinforcement ribs to the mesh. The ribs can be molded into and as part of the mesh sheet or can be attached to the mesh during an assembly operation. If the ribs are incorporated along lines 38A and 38B in FIGS. 1 and 2, once the suture is tensioned to fold the mesh sheet, the ribs would keep the site from compressing along the axis of line 38A or 38B. The connection structure also controls the direction of loads from the mesh sheet into the attached tissue by allowing control of the attachment mechanism and these applications. Compression members may be designed into these ribs to allow the final configuration to flex into a three dimensional shape that is controllable. An example of this would be that the structural rib allows the edges of the mesh to be formed into a sleeve with the internal diameter held open. This way the sleeve is prevented from collapsing on itself. These compression members can be molded into the mesh sheet in such a way that the mesh sheet itself folds into a pre designed shape. Living hinge type joints 150 incorporated into the mesh sheet 112 would also allow controlled flexure in the desired shape. See FIGS. 19A and 19B for examples of mesh sheet flexure shown up in an initial position in FIG. 19A and a secondary position in FIG. 19B.

It is further contemplated the concepts underlying the present invention can be used to simplify wound closure. In accordance with such an embodiment, the sheet can be adhered to the skin on the outside edges of a wound using adhesives, tapes, or other suitable means. The tensioning members within the mesh sheet is then tightened bringing the wound together. The mesh sheet might contain healing agents or a coating of such agents. The advantages of this system are that the wound could be large with missing tissue and this mesh sheet allows even compression around the wound to bridge the gap between the large defect area. Steri strips might not be used if large areas of tissue are missing. The mesh sheet can extend out over a large defect without issue. The mesh sheet for this application might need to be absorbable such that removal is not necessary. A healing agent built into this mesh sheet can help hold the remaining tissue together and aligned while healing takes place. This basic means of approximating tissues may also be more generally applied to the closure of any otomy or perforation in or on the body.

In accordance with yet a further embodiment, and with reference to FIGS. 22, 23, 24 and 25, a tensioning system 310 employs a zipper/suture gathering mechanism. In practice, the tensioning system 310 includes a base material composed of a sheet of material 312 having a football shaped central open 350. The sheet of material includes opposed external edges 318, 320 which are connected at their respective ends 318a, 318b, 320a, 320b to define the central opening 350. The external edges 318, 320 are shaped and dimensioned for attachment to the gastric cavity wall for drawing the secured tissue portions together in a manner creating a fold 334. As discussed, in its untensioned configuration as shown with reference to FIGS. 22 and 24, the tensioning system 310 includes a football shaped opening 350. The opening 350 includes a first end 352 and second end 354 which are substantially closed. Between the first end 352 and the second end 354 the central opening 350 extends outwardly such that the largest opening diameter as the opening 350 extends between the first end 352 and the second end 354 is at a position substantially midway between the first end 352 and the second end 354 of the tensioning system 310. The external edges 318, 320 of the tensioning system 310 may be affixed to the gastric cavity by a suture, staples, adhesive or other mechanism. Once affixed, the opening 350 is closed by either a zipper 360 (see FIGS. 22 and 23) or suture tensioning weave 362 (see FIGS. 24 and 25) that extends between the first and second sides 364, 366 of the tensioning system 310. In this way, the tissue of the gastric cavity is gathered to create a fold along the wall of the gastric cavity, reducing the volume inside the gastric cavity and creating satiety with less food intake. Ultimately, the reduction in gastric cavity volume will result in weight loss.

Figure 22:
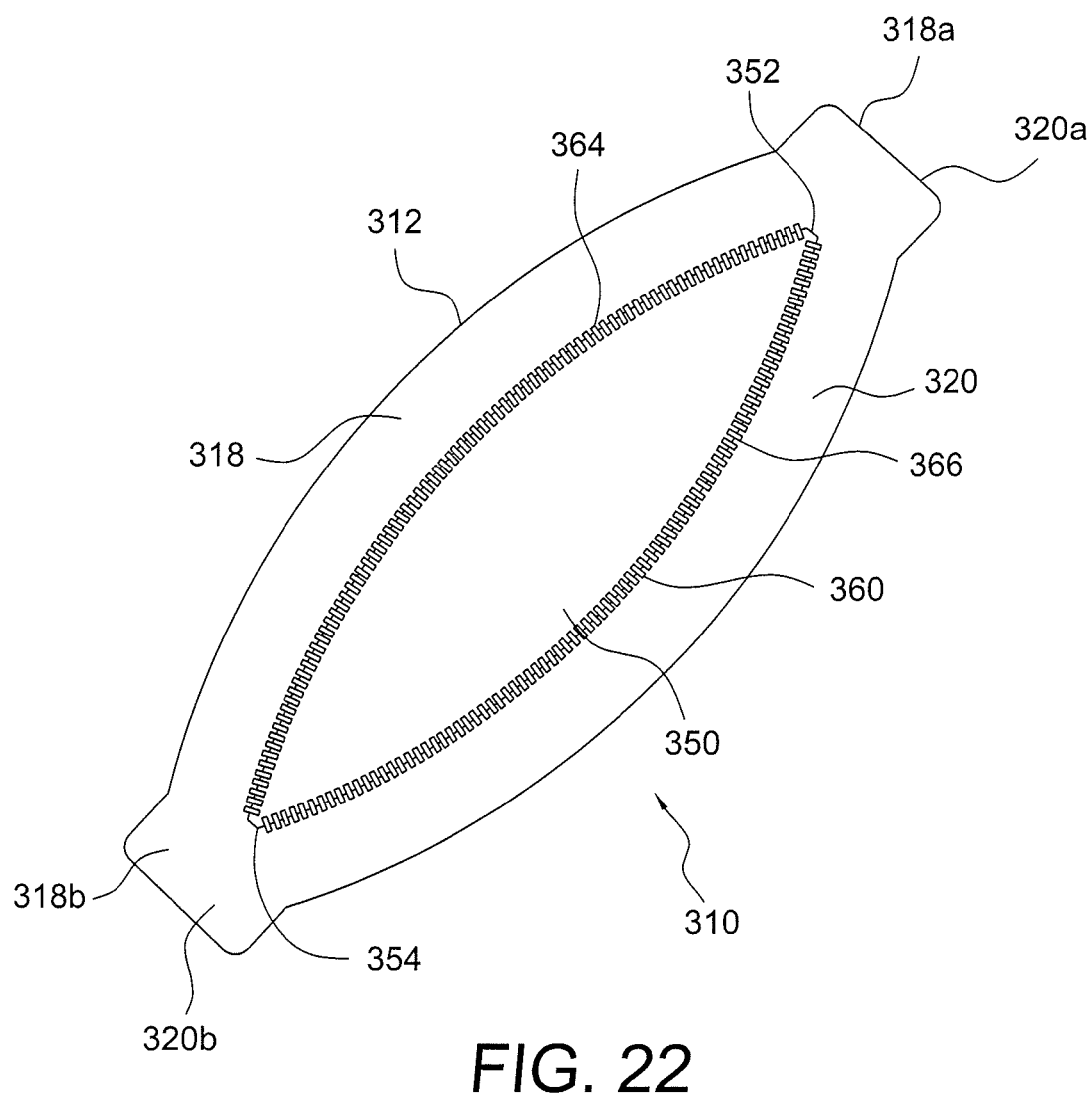
FIGS. 22, 23, 24 and 25 show implementation of an alternate tensioning system in accordance with the present invention.
Figure 23:
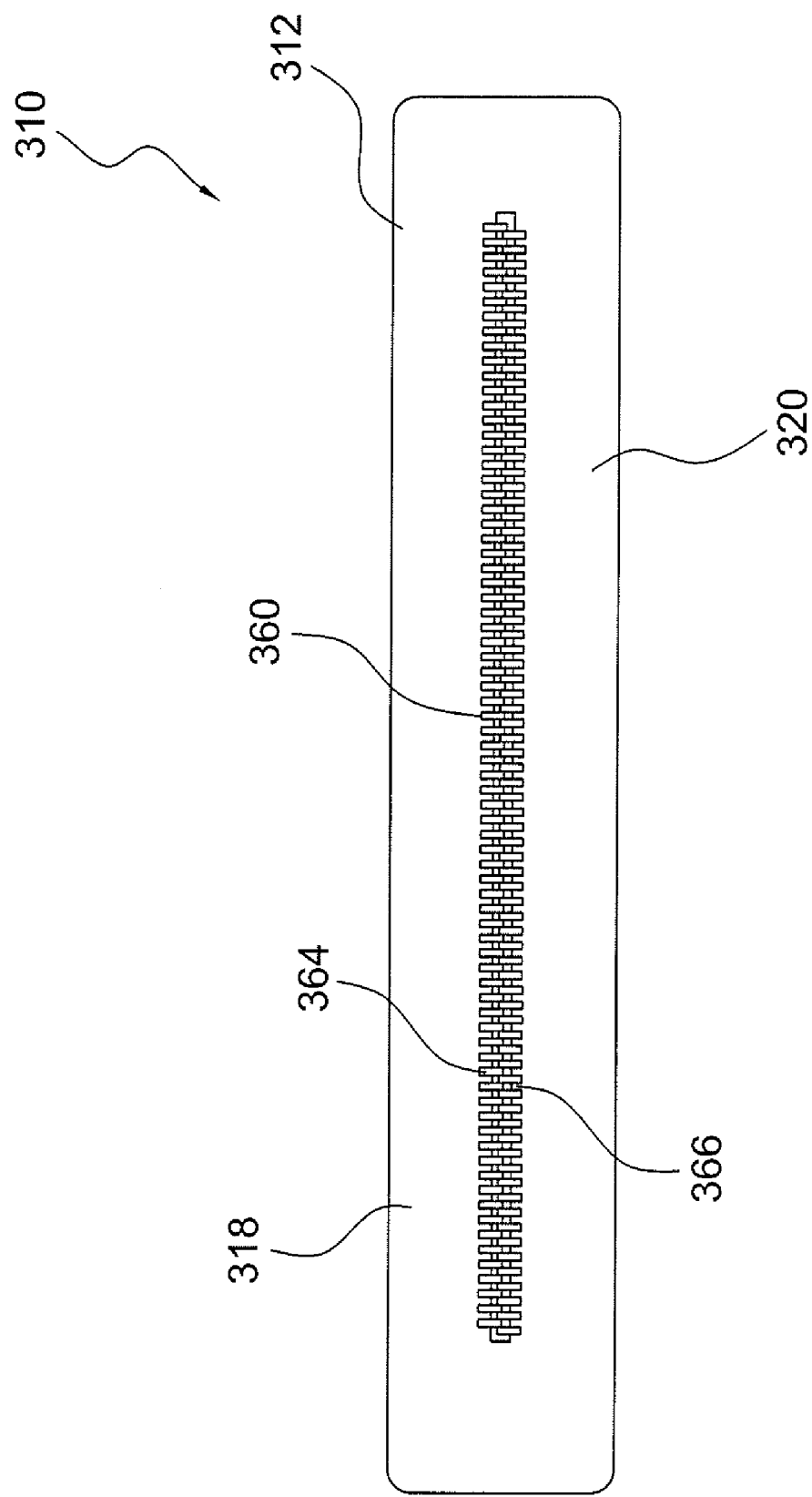
Figure 24:
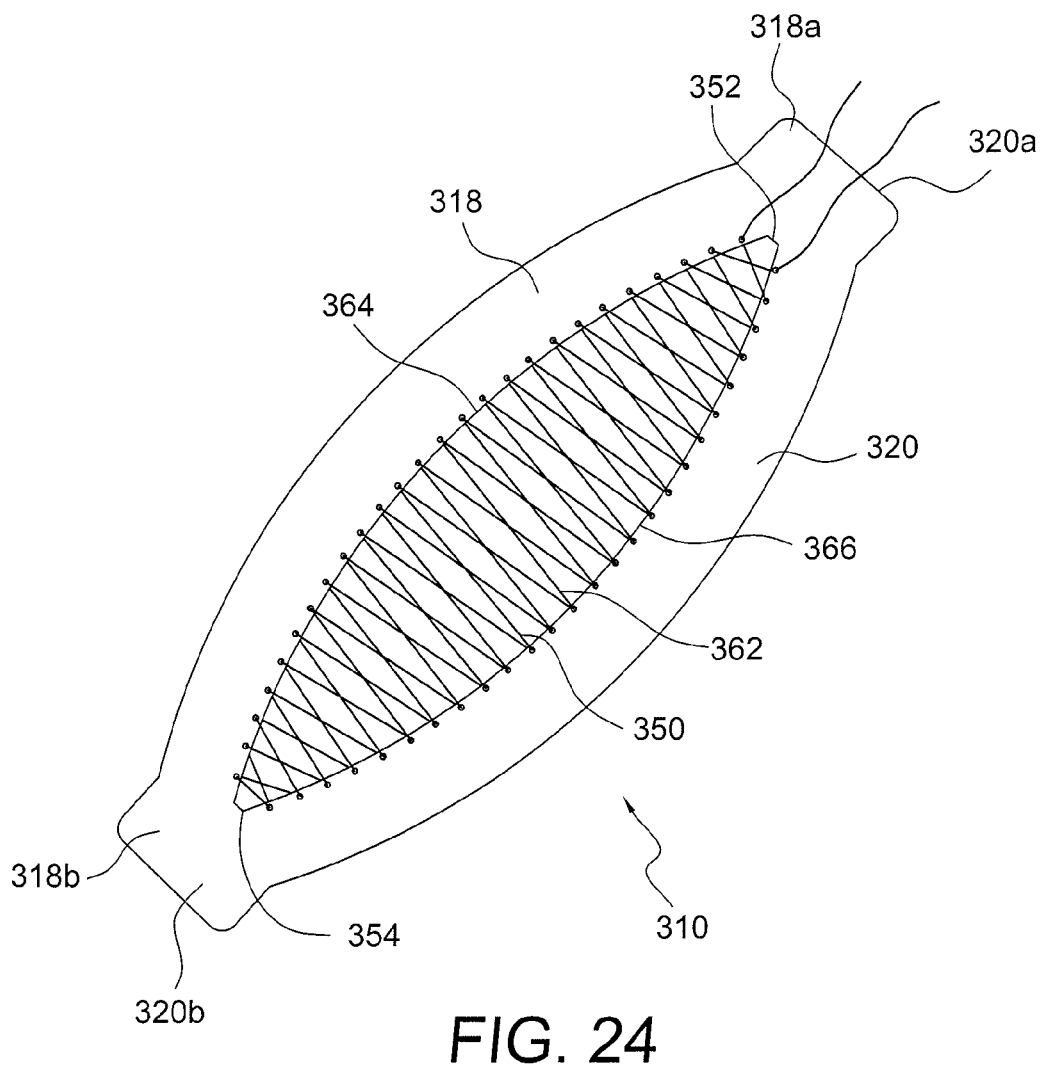
Figure 25:
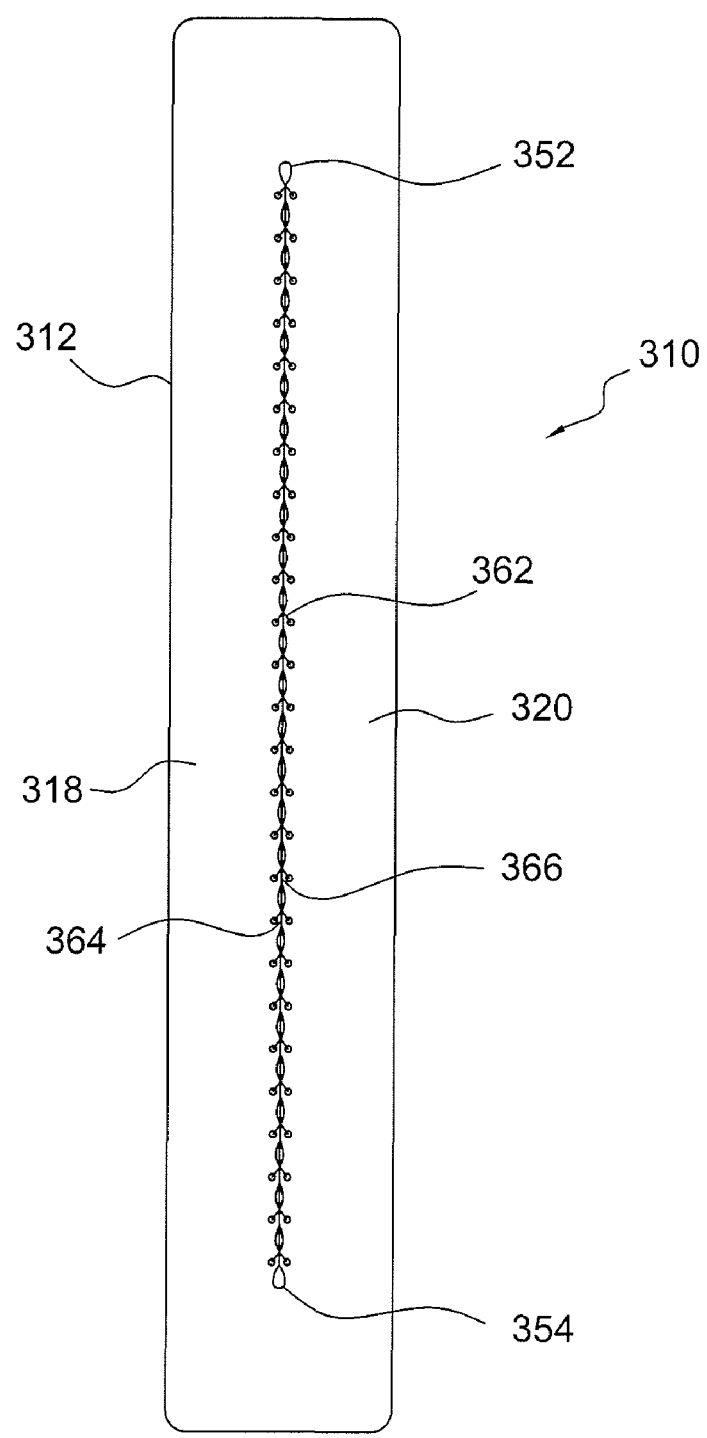
Figure 26:
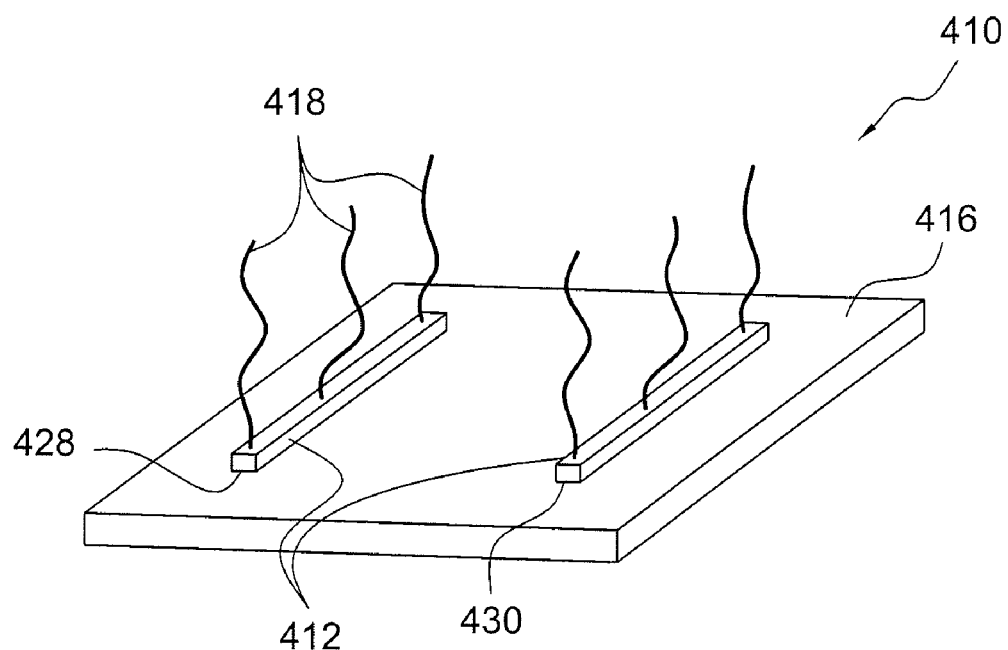
FIGS. 26 and 27 show another embodiment of a tensioning system in accordance with the present invention.
Figure 27:
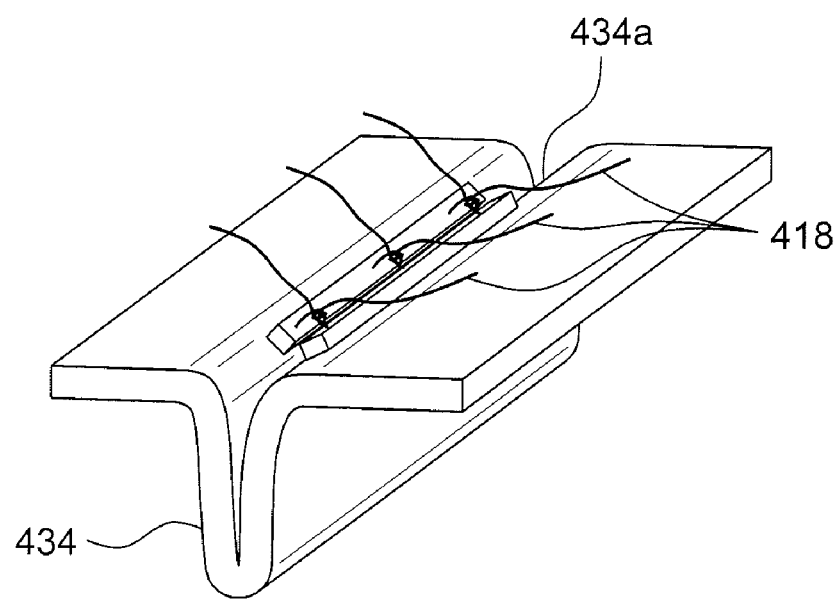
Figure 28:
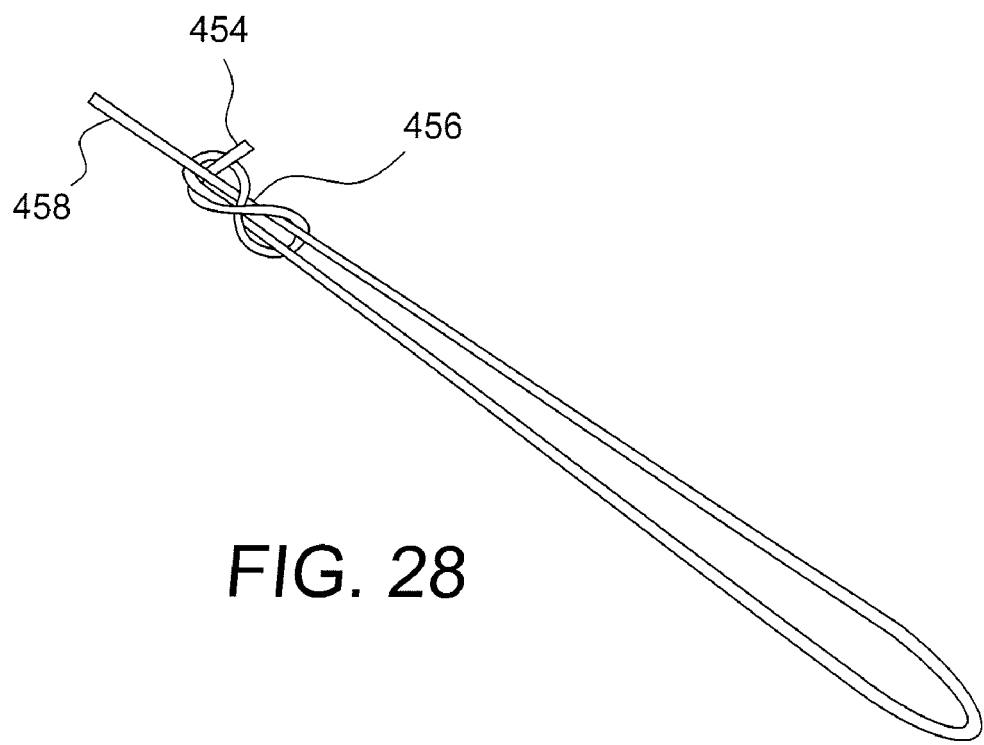
FIGS. 28 and 29 show a knotting structure for use in accordance with the embodiment shown in FIGS. 26 and 27.
Figure 29:
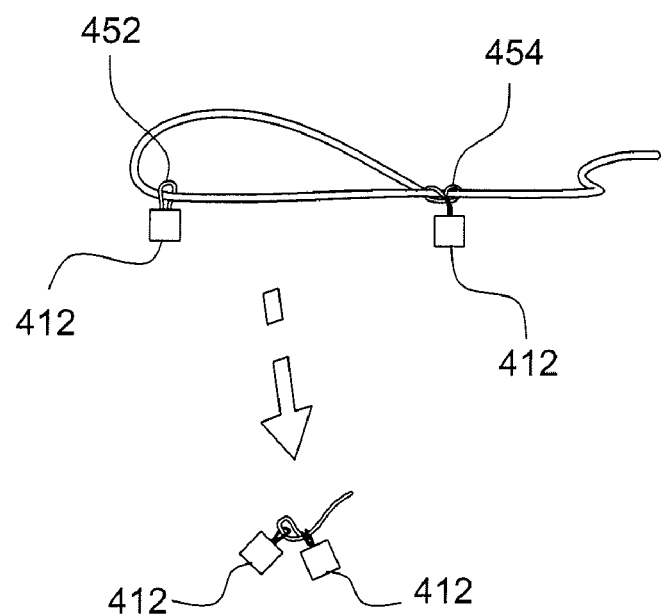

In operation, and with reference to FIGS. 22 and 23, FIG. 22 shows the tensioning system 310 with the zipper 360 unzipped and the opening 350 fully open. This is the orientation in which the tensioning system 310 is secured to the wall of the gastric cavity. Once it is desired to create a fold, the zipper 360 is pulled to activate the zipper and pull the first and second sides 364, 366 of the tensioning member 310 together drawing the secured tissue together. Similarly, and with reference to FIGS. 24 and 25, FIG. 24 shows the tensioning system 310 with the suture tensioning weave 362 loosed and the opening 350 fully open. This is the orientation in which the tensioning system 310 is secured to the wall of the gastric cavity 316. Once it is desired to create a fold, the suture tensioning weave 362 is tensioned to pull the first and second sides 364, 366 of the tensioning member 310 together drawing the secured tissue together.

In accordance with yet a further embodiment, and with reference to FIGS. 26, 27, 28 and 29, a tensioning system 410 is provided by securing ribs 412 along opposite sides along a length of tissue, for example, the gastric cavity 416. In accordance with a preferred embodiment, the ribs 412 are elongated members and are oriented along the tissue in a substantially parallel manner. Secured between the ribs 412 are a series of tensioning members 418. The tensioning members 418, in accordance with a preferred embodiment, are simply sutures that may be tied once the tissue to which the ribs 412 are secured is drawn together in a desired manner. With the sutures tied, the tissue is held is a desired folded configuration.

It is further contemplated, the sutures may be attached with pre-tied knots, pre-loaded knotting elements, zip ties, or other tying mechanisms. In accordance with a preferred embodiment, ties may be created as disclosed in FIGS. 28 and 29. More particularly, loop 450 is passed through an eyelet 452 on one rib 412. The tail 454 of the knot 456 is then fixed to the other rib 412. Thereafter, the suture 420 may be tensioned and the tissue drawn in apposition along the various fold lines. In practice, the ribs 412 are delivered to the site and sheaths surrounding the ribs 412 for deployment are removed. Thereafter, the first rib 412 is secured to a first edge 428 of a fold line 434a to be created. The rib 412 is secured thereto with staples, adhesives or other suitable fastening mechanism. For this system to work, the tail 454 of knot 456 must be attached to the ribs 412. The tail 454 is the shorter of the two strands that extend from the knot. As such, when the rib 412 pulls on the tail 454, it tightens the knot 426 preventing slippage of the longer suture 458 that allows the loop size to grow. It is contemplated it may be desirable to mechanically, chemically, thermally, or otherwise treat the tissue to induce healing upon completion of the procedure. Thereafter, the second rib 412 is secured to the second edge 430 of the fold 434 to be created. The prettied knot 456 is preferably used to cinch the system together in accordance with this embodiment. However, knotting elements may be utilized to secure the system in accordance with an alternate embodiment. Once the fold 434 is created by cinching the ribs 412 together, fixation means, for example, adhesives, EMS type box/skin staplers and/or bar/tissue securing devices may be secured on the rib to hold the fold in a desired configuration for long term fixation. It is contemplated the present procedure is preferably desirable for gastric plications wherein the ribs are applied to the external surface of the stomach; gastric plications where the device is delivered transorally or transgastrically; and gastroplasty procedures where the device is delivered transorally/transgastrically and one rib is secured to the anterior surface of the stomach and the other rib is secured to the posterior surface of the stomach.

In accordance with yet a further, hybrid gastric volume reduction entails making plications in the stomach for the purpose of volume reduction. The surface area and volume of the stomach are reduced, thereby, in theory, reducing portion size consumed to satiate a patient. Current appliers are single shot and multi-clip appliers which require a large amount of work to place a line series of plications. Variability is bound to be high and repeatability is virtually non-existent. Since stability is important to early healing, a regular line of fasteners is advantageous. In addition, there is a premium on speed and a minimum number of instruments for insertion and extraction is, therefore, desirable.

In accordance with a preferred embodiment, the present invention utilizes a liner multiple ring applier with prewoven fasteners, for example, as disclosed with reference to commonly owned U.S. Patent Application Publication No. 2007/0276409 to Ortiz et al., entitled "Endoscopic Gastric Reduction Methods and Apparatus", which is incorporated herein by reference. The device may be quickly lay down upon opposed plication line which may then be cinched together by the suture material prethreaded with the fasteners employed with the disclosed apparatus. In practice, one region of the hollow body organ (for example, the gastric cavity) is acquired through the application of aligned rings on the extension surface of the gastric cavity in accordance the '409 publication. Thereafter, the other region, of the gastric cavity is acquired for the application of aligned rings in accordance with the '409 publication. Since the rings are prethreaded with suture material, subsequent cinching is accomplished after removal of the applier device for the creation of a fold. The present embodiment provides for rapid application of a long straight line of fasteners, repeatability, high reliability, low force application, verifiability and reversibility.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the invention described herein will be processed before surgery. First, a new or used system is obtained and if necessary cleaned. The system can then be sterilized. In one sterilization technique, the system is placed in a closed and sealed container, such as a plastic or TYVEK, a flexible sheet made of polyethylene fibers, bag. The container and system are then placed in a field of radiation that can penetrate the container, such as gamma radiation, x-rays, or high-energy electrons. The radiation kills bacteria on the system and in the container. The sterilized system can then be stored in the sterile container. The sealed container keeps the system sterile until it is opened in the medical facility.

It is preferred that the device is sterilized. This can be done by any number of ways known to those skilled in the art including beta or gamma radiation, ethylene oxide, or steam.

While the preferred embodiments have been shown and described, it will be understood that there is no intent to limit the invention by such disclosure, but rather, is intended to cover all modifications and alternate constructions falling within the spirit and scope of the invention.

The invention claimed is:

1. A method for restricting available volume of a gastric cavity, comprising:
   providing a tension system comprising a sheet including a first edge and a second edge;
   securing the first edge of the sheet to the gastric cavity along a first line and securing the second edge of the sheet to the gastric cavity along a second line;
   drawing the first and second edges of the sheet toward each other so as to draw the first line toward the second line thereby creating a fold in the tissue between the first line and the second line.

2. The method according claim 1, wherein the tension system includes tensioning members coupled to the sheet.

3. The method according claim 2, wherein the tensioning members are strings that are parallel to one another and spaced along the sheet such that each of the tensioning members principally extends along either a length or width of the sheet.

4. The method according claim 2, wherein each of the tensioning members is woven within the sheet such that a woven central portion of the tensioning members is free to move relative to the sheet.

5. The method according claim 4, wherein each of the tensioning members is woven so as to extend from one side of the sheet with a first end and a second end of the tensioning members extending from opposite sides of the sheet such that pulling upon either or both of the first end and the second end will cause the first and second edges of the sheet to be drawn together.

\* \* \* \* \*